(12) United States Patent
Hauger et al.

(10) Patent No.: US 9,044,142 B2
(45) Date of Patent: Jun. 2, 2015

(54) SURGICAL OPTICAL SYSTEMS FOR DETECTING BRAIN TUMORS

(75) Inventors: Christoph Hauger, Aalen (DE); Guido Hattendorf, Phoenix, AZ (US); Peter Maxwell Delaney, Carnegie (AU); Robert F. Spetzler, Paradise Valley, AZ (US); Mark C. Preul, Scottsdale, AZ (US); Jennifer Eschbacher, Phoenix, AZ (US); Peter Nakaji, Phoenix, AZ (US)

(73) Assignee: Carl Zeiss Meditec AG, Jena (DE)

( * ) Notice: Subject to any disclaimer, the term of this patent is extended or adjusted under 35 U.S.C. 154(b) by 337 days.

(21) Appl. No.: 13/043,120

(22) Filed: Mar. 8, 2011

(65) Prior Publication Data

US 2011/0280810 A1    Nov. 17, 2011

Related U.S. Application Data

(60) Provisional application No. 61/313,268, filed on Mar. 12, 2010.

(51) Int. Cl.
| | |
|---|---|
| *A61B 6/00* | (2006.01) |
| *A61B 5/00* | (2006.01) |
| *A61B 1/04* | (2006.01) |
| *G02B 21/00* | (2006.01) |
| *A61B 1/00* | (2006.01) |
| *A61B 1/313* | (2006.01) |
| *A61B 19/00* | (2006.01) |

(52) U.S. Cl.
CPC ........... *A61B 5/0068* (2013.01); *A61B 1/00188* (2013.01); *A61B 1/043* (2013.01); *A61B 1/313* (2013.01); *A61B 19/5223* (2013.01); *G02B 21/0052* (2013.01)

(58) Field of Classification Search
None
See application file for complete search history.

(56) References Cited

U.S. PATENT DOCUMENTS

| | | | |
|---|---|---|---|
| 6,319,682 B1 * | 11/2001 | Hochman | 435/29 |
| 6,564,087 B1 * | 5/2003 | Pitris et al. | 600/478 |
| 6,567,585 B2 * | 5/2003 | Harris | 385/33 |
| 6,573,063 B2 * | 6/2003 | Hochman | 435/29 |
| 6,671,540 B1 * | 12/2003 | Hochman | 600/431 |
| 7,019,309 B2 * | 3/2006 | Gu et al. | 250/458.1 |
| 7,267,647 B2 * | 9/2007 | Okada et al. | 600/166 |
| 7,330,305 B2 * | 2/2008 | Harris | 359/368 |
| 7,330,747 B2 * | 2/2008 | Maier | 600/322 |

(Continued)

FOREIGN PATENT DOCUMENTS

| | | |
|---|---|---|
| WO | WO 01/50955 | 7/2001 |
| WO | WO 2008/093528 | 8/2008 |

OTHER PUBLICATIONS

Martirosyan et al, "Use of in vivo near-infared laser confocal endomicroscopy with indocyanine green to detect the boundary of infiltrative tumor," J Neurosurg 115: 1131-1138, 2011.*

(Continued)

*Primary Examiner* — Nicholas Evoy
(74) *Attorney, Agent, or Firm* — Fish & Richardson P.C.

(57) ABSTRACT

A method of detecting a brain tumor includes administering indocyanine green to a living body; exposing brain tissue in the living body; irradiating the exposed brain tissue with excitation light of indocyanine green; obtaining an image based on fluorescence of the excited indocyanine green in the brain tissue, wherein the image is obtained using an endomicroscope; and identifying portions of the brain tissue corresponding to the brain tumor based on the image.

27 Claims, 6 Drawing Sheets

(56) References Cited

U.S. PATENT DOCUMENTS

| | | | |
|---|---|---|---|
| 7,350,920 B2* | 4/2008 | Levine | 351/206 |
| 7,369,073 B2* | 5/2008 | Jess et al. | 341/139 |
| 7,394,053 B2* | 7/2008 | Frangioni et al. | 250/208.1 |
| 7,580,185 B2* | 8/2009 | Haisch et al. | 359/385 |
| 8,040,599 B2* | 10/2011 | Steffen et al. | 359/388 |
| 8,189,201 B2* | 5/2012 | Haisch et al. | 356/497 |
| 8,287,126 B2* | 10/2012 | Hauger et al. | 351/246 |
| 8,300,309 B2* | 10/2012 | Haisch et al. | 359/385 |
| 8,306,600 B2* | 11/2012 | Steffen et al. | 600/407 |
| 8,320,650 B2* | 11/2012 | Demos et al. | 382/128 |
| 8,705,042 B2* | 4/2014 | Haisch et al. | 356/456 |
| 8,773,760 B2* | 7/2014 | Gmitro et al. | 359/385 |
| 8,810,907 B2* | 8/2014 | Haisch et al. | 359/388 |
| 8,838,213 B2* | 9/2014 | Tearney et al. | 600/478 |
| 2004/0061072 A1* | 4/2004 | Gu et al. | 250/458.1 |
| 2004/0076390 A1* | 4/2004 | Dong Yang et al. | 385/116 |
| 2004/0109231 A1* | 6/2004 | Haisch et al. | 359/385 |
| 2005/0174425 A1* | 8/2005 | Harris | 348/45 |
| 2006/0108509 A1* | 5/2006 | Frangioni et al. | 250/208.1 |
| 2006/0134001 A1* | 6/2006 | Frangioni | 424/9.6 |
| 2007/0090985 A1* | 4/2007 | Jess et al. | 341/155 |
| 2007/0121196 A1* | 5/2007 | Tearney et al. | 359/333 |
| 2008/0007693 A1* | 1/2008 | Williams et al. | 351/221 |
| 2008/0013166 A1* | 1/2008 | Haisch et al. | 359/353 |
| 2008/0097198 A1* | 4/2008 | Miwa et al. | 600/431 |
| 2008/0097225 A1* | 4/2008 | Tearney et al. | 600/478 |
| 2008/0240535 A1* | 10/2008 | Frangioni et al. | 382/131 |
| 2009/0203994 A1* | 8/2009 | Mangat et al. | 600/433 |
| 2009/0285760 A1* | 11/2009 | Ishikawa et al. | 424/9.3 |
| 2009/0326359 A1* | 12/2009 | Hendriks et al. | 600/407 |
| 2010/0044583 A1* | 2/2010 | Steffen et al. | 250/458.1 |
| 2010/0097618 A1* | 4/2010 | Haisch et al. | 356/503 |
| 2010/0110538 A1* | 5/2010 | Steffen et al. | 359/363 |
| 2010/0134605 A1* | 6/2010 | Demos et al. | 348/65 |
| 2011/0004098 A1* | 1/2011 | Danikas et al. | 600/435 |
| 2011/0015529 A1* | 1/2011 | Abrat et al. | 600/478 |
| 2011/0168914 A1* | 7/2011 | Haisch et al. | 250/459.1 |
| 2011/0261367 A1* | 10/2011 | Gmitro et al. | 356/479 |
| 2011/0280810 A1* | 11/2011 | Hauger et al. | 424/9.6 |
| 2012/0019777 A1* | 1/2012 | Hauger et al. | 351/206 |
| 2012/0194663 A1* | 8/2012 | Haisch et al. | 348/77 |
| 2012/0220870 A1* | 8/2012 | Gambhir et al. | 600/431 |
| 2012/0249771 A1* | 10/2012 | Haisch et al. | 348/79 |
| 2013/0066215 A1* | 3/2013 | Tearney et al. | 600/478 |
| 2013/0271757 A1* | 10/2013 | Kang et al. | 356/300 |
| 2014/0154717 A1* | 6/2014 | Yamada et al. | 435/14 |
| 2014/0213899 A1* | 7/2014 | Danikas et al. | 600/435 |

OTHER PUBLICATIONS

Martirosyan et al., Use of in vivo near-infrared laser confocal endomicroscopy with indocyanine green to detect the boundary of infiltrative tumor, J Neurosurg 115:1131-1138, 2011.*

Raabe et al., Near-Infrared Indocyanine Green Video Angiography: A New Method for Intraoperative Assessment of Vascular Flow, Neurosurgery 52:132-139, 2003.*

Sankar et al., Miniaturized Handheld Confocal Microscopy for Neurosurgery: Results in an Experimental Glioblastoma Model, Neurosurgery 66:410-418, 2010.*

Soo-Ping Thong et al., Laser confocal endomicroscopy as a novel technique for fluorescence diagnostic imaging of the oral cavity, Journal of Biomedical Optics 12(1), 014007, Jan./Feb. 2007.*

Zehri et al., Neurosurgical confocal endomicroscopy: A review of contrast agents, confocal systems, and future imaging modalities, Surgical Neurology International 2014, 5:60.*

P. Y. Wen et al., *N Engl J Med* 2008;359:492-507 (Jul. 31, 2008).

A. Raabe et al., *Neurosurgery* 52, 132 (Jan. 2003).

D. Zagzag et al., Lab Invest 80, 837 (Jun. 2000).

Delaney and Harris, *Handbook of Biological Confocal Microscopy*, Third Edition, edited by James B. Pawley, Springer Science + Business Media, LLC, New York, 2006, pp. 501-515.

G. R. Cherrick et al., *J Clin Invest* 39, 592 (Apr. 1960).

I. Roberts et al., *Lancet* 342, (1993).

J. V. Frangioni, *Current Opinion in Chemical Biology* 2003, 7:626-634 (Oct. 2003).

K. J. Baker, *Proc Soc Exp Biol Med* 122, 957 (Aug.-Sep. 1966).

M. Candolfi et al., *J Neurooncol* (2007) 85:133-148 (Nov. 2007).

M. Lacroix et al., *J Neurosurg* 95: 190-198, 2001 (Aug. 2001).

M. M. Haglund et al., *Neurosurgery*, vol. 38, No. 2, Feb. 1996 (Feb. 1996).

R. Kiesslich et al., *Gastroenterology* vol. 127, No. 3 (2004).

T. Szatmari et al., Cancer Sci 97, 546 (Jun. 2006).

W. Stummer et al., *The Lancet Oncology* 2006; 7: 392-401 (2006).

* cited by examiner

SURGICAL OPTICAL SYSTEMS FOR DETECTING BRAIN TUMORS

CROSS-REFERENCE TO RELATED APPLICATIONS

This application claims priority to Provisional Application No. 61/313,268, entitled "INDOCYANINE GREEN USE FOR DETECTING BRAIN TUMORS," filed on Mar. 12, 2010, the entire contents of which are incorporated herein by reference.

BACKGROUND

Each year approximately 16,000 new adult brain tumors are diagnosed in the United States (see, e.g., P. Y. Wen, S. Kesari, N Engl J Med 359, 492 (Jul. 31, 2008)). Cytoreduction, verification of histology, and identification of tumor invasion in macroscopically normal-appearing tissue are crucial to predict prognosis (see, e.g., M. Lacroix et al., J Neurosurg 95, 190 (August, 2001)). Unlike in other organ systems, complete resection of cancer in the brain is often not possible because of tumor cell infiltration and the goal to preserve brain tissue. Furthermore, discerning among gliosis, radiation effects, and tumor-containing tissue after a recurrence can be difficult. The current neurosurgical armamentarium for guiding tumor resection is based on macroscopic identification of tumor region and does not result in complete resection and clearance of surgical margins. Frozen sections are time-consuming and often do not reveal the histologic features needed for final diagnosis when compared with permanent sections. An optimal imaging technique would allow intraoperative identification of regions containing tumor and their microscopic extent, producing real-time data that enhances ongoing surgical decisions without significantly prolonging anesthesia and operative times.

Fluorescence imaging approaches to these challenges have been developed. 5-aminolevulinic acid is used for visible wavelength fluorescence (VWF) imaging at operating microscope magnification during glioma surgery (see, e.g., W. Stummer et al., The Lancet Oncology 7, 392 (2006)).

SUMMARY

Verification of histology and identification of tumor invasion in macroscopically normal-appearing brain tissue determine prognosis in resection of malignant gliomas. Complete resection of brain cancer is often not possible because of tumor cell infiltration and the goal to preserve brain tissue. Indocyanine green induces fluorescence of tumor cells detected by intraoperative confocal endomicroscopy in the near infrared wavelength. Individual tumor cells within brain tissue were identified within 475×475 µm field of view and a definitive tumor border delimited. Endomicroscopy greatly enhanced the interpretation of the macroscopic observations by providing real-time histological information precisely related to the site of microscopic imaging. These results may dramatically increase the completeness of tumor resection and thereby improve the outcomes of patients with infiltrative brain tumors.

In general, in a first aspect, the invention features a method, including introducing indocyanine green into a patient; and using confocal microscopy to detect a tumor in brain tissue of the patient based on fluorescence from the indocyanine green.

Implementations of the method can include one or more of the following features. For example, the confocal microscopy can be performed using an endomicroscope.

The method can include using a surgical microscope to observe the brain tissue concurrently to using the confocal microscopy.

The method can include performing surgery on the brain tissue concurrently to using the confocal microscopy.

Detecting the tumor can include identifying individual tumor cells using the confocal microscopy.

Using confocal microscopy can include illuminating the brain tissue with radiation. The radiation can be near infrared (NIR) radiation. The radiation can include wavelengths in a range from 600 nm to 900 nm.

Detecting the tumor can include imaging the brain tissue at an emission wavelength of indocyanine green. Detecting the tumor can include identifying individual tumor cells based on fluorescence from the indocyanine green in the brain tissue. Detecting the tumor can include delimiting a border of the tumor based on fluorescence from the indocyanine green in the brain tissue.

In another aspect, the invention features a method, including introducing indocyanine green into a patient; and identifying margins of a tumor in brain tissue of the patient based on fluorescence from the indocyanine green using microscopy that resolves individual tumor cells. Implementations of the method can include one or more of the features mentioned above with respect to the first aspect.

In another aspect, the invention features a method, including introducing indocyanine green into a patient; using confocal endomicroscopy to detect a tumor in brain tissue of the patient based on fluorescence from the indocyanine green; using a surgical microscope to observe the brain tissue concurrently to using the confocal microscopy; and performing surgery on the brain tissue concurrently to using the confocal microscopy. Implementations of the method can include one or more of the features mentioned above with respect to the first aspect.

In another aspect, the invention features a method of detecting a brain tumor, including administering indocyanine green to a living body; exposing brain tissue in the living body; irradiating the exposed brain tissue with excitation light of indocyanine green; obtaining an image based on fluorescence of the excited indocyanine green in the brain tissue, wherein the image is obtained using an endomicroscope; and identifying portions of the brain tissue corresponding to the brain tumor based on the image. Implementations of the method can include one or more of the features mentioned above with respect to the first aspect.

In general, in a further aspect, the invention features a microscopy system, including a first microscope having a first field of view configured to acquire images of a sample within the first field of view based on infrared radiation; a second microscope having a second field of view configured to acquire images of the sample within the second field of view, where an area of the second field of view is at least an order of magnitude smaller than an area of the first field of view; a navigation sub-system configured to monitor a location of the second microscope; and a display sub-system in communication with the first microscope, the second microscope and the navigation sub-system, wherein during operation the display sub-system displays information about a relative location of one or more images acquired using the second microscope relative to the field of view of the first microscope based on information from the navigation sub-system.

Embodiments of the system can include one or more of the following features and/or features of other aspects. For example, the first microscope can be a surgical microscope. The first microscope can have a field of view having an area of 1 cm$^2$ or more (e.g., 2 cm$^2$ or more, 5 cm$^2$ or more).

The first microscope can include an infrared camera.

The first microscope can be configured to acquire images of the sample within the first field of view based on visible radiation in addition to infrared light.

The first microscope can be a fluorescence microscope. The first microscope can be configured to detect radiation at wavelengths of 800 nm or more (e.g., from 800 nm to 850 nm). The first microscope can be configured to detect radiation at one or more wavelengths corresponding to fluorescence wavelengths of indocyanine green. The first microscope can include a camera and a filter positioned in an optical path between the sample and the detector, the filter being configured to transmit radiation at one or more wavelengths corresponding to fluorescence wavelengths of indocyanine green.

The first microscope can include a radiation source configured to illuminate the sample with radiation at a wavelength corresponding to an absorption wavelength of indocyanine green.

The second microscope can be an endomicroscope. The second microscope can be a confocal microscope. The second microscope can be a confocal endomicroscope.

The second microscope can include a detector and a bundle of optical fibers configured to deliver radiation from the sample to the detector. The second microscope can include a hand-held probe arranged to allow a user to position an end of the bundle at different locations of the sample.

The area of the field of view of the second microscope can be 1 mm$^2$ or less (e.g., 0.5 mm$^2$ or less, 0.3 mm$^2$ or less, 0.2 mm$^2$ or less, 0.1 mm$^2$ or less).

The second microscope can be a fluorescence microscope. The second microscope can be configured to detect radiation at wavelengths of 800 nm or more (e.g., from 800 nm to 850 nm). The second microscope can be configured to detect radiation at one or more wavelengths corresponding to fluorescence wavelengths of indocyanine green.

The sample can be a tissue sample and the second microscope has a resolution sufficient to resolve individual cells in the sample.

The navigation sub-system can include one or more probes attached to the second microscope and a tracking module that monitors a location of the one or more probes.

The display sub-system can be configured to simultaneously display one or more image of the sample from the first microscope and one or more image of the sample from the second microscope.

The display sub-system can be configured to display locations in an image acquired by the first microscope where images were acquired using the second microscope based on information from the navigation sub-system.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4(A) Macroscopically visible tumor with NIR light, delineated by an intense, heterogeneous central fluorescent region and a less bright peripheral halo one minute after ICG injection (left). Intensity of fluorescence in the central region of tumor increased at 15 minutes after injection. Regions of focal brightness, morphologically consistent with normal brain on confocal endomicroscopy, mostly representing leakage of ICG related to surgical trauma (arrow) (right). FIG. 4(B) Immediately after ICG injection, fluorescence was visible only in few clusters of tumor cells (left). Fifteen minutes after ICG injection, the entire tumor mass was saturated with ICG, expressing bright fluorescence of tumor cells (right).

Like reference symbols in the various drawings indicate like elements.

DETAILED DESCRIPTION

Indocyanine green (ICG) can be used in combination with a microscope (e.g., an endomicroscope) for the detection of brain tumors.

Figure 1:
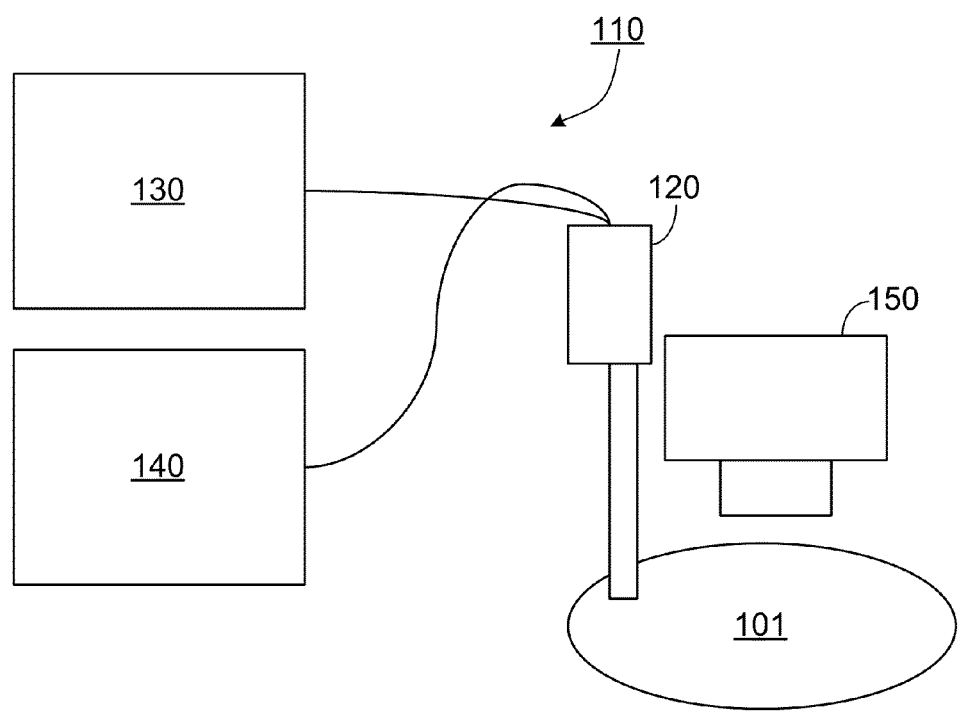
FIG. 1 is a schematic diagram of an embodiment of a microscopy system.
Figure 2:
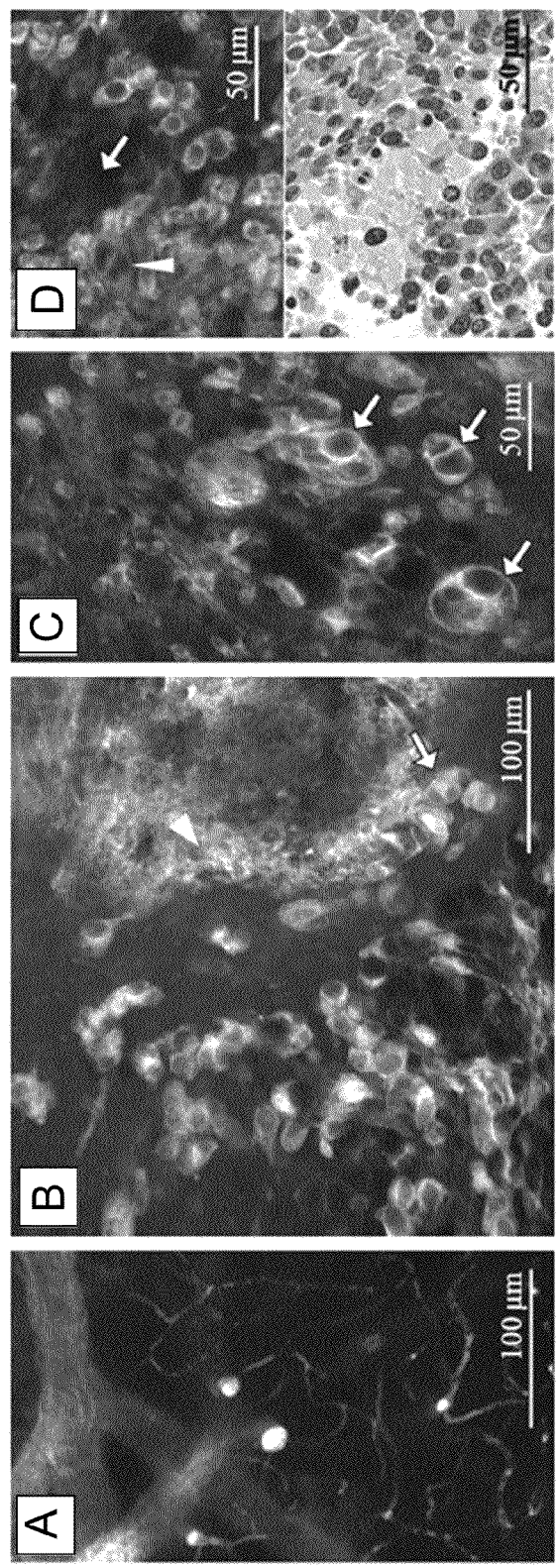
FIG. 2(A) shows confocal images of normal brain area obtained with an endomicroscope demonstrate predominantly intravascular ICG distribution, fluorescent small vessels and capillary networks. Individual erythrocytes are visible within capillaries. Scale bar, 100 μm.
FIG. 2(B) shows confocal images obtained during scanning of the operative bed demonstrate infiltrative tumor (arrows) into adjacent edematous brain parenchyma (arrowhead) consistent with residual tumor and positive surgical margins. Scale bar, 100 μm.
FIG. 2(C) shows images obtained with the handheld miniaturized confocal endomicroscope using ICG reveal the atypical morphologic features of tumor cells, including pleomorphic enlarged nuclei, mitoses and multinucleated cells (arrows). Scale bar, 50 μm.
FIG. 2(D) shows confocal images obtained during surgery highlight cellular tumor with necrosis (arrow) and mitosis (arrowhead) (top). Hematoxylin and eosin section (×400) from the same imaging region of interest reveals corresponding histologic characteristics (bottom). Scale bars, 50 μm.

Referring to FIG. 1, a microscopy system for use during brain surgery includes a confocal endomicroscope 110 and a surgical microscope 150, both arranged to view brain tissue 101 of a patient who has been injected (e.g., intravenously) with ICG. Generally, confocal endomicroscope 110 has higher resolution that surgical microscope 150. For example, in some embodiments, confocal endomicroscope 110 can resolve individual brain cells, while surgical microscope 150 cannot. A surgeon uses surgical microscope to identify tumor tissue on a macroscopic level. During resection of the tumor tissue, the surgeon can use confocal endomicroscope 110 to accurately identify tumor margins. In other words, the surgeon uses confocal endomicroscope to perform optical biopsies of the brain tissue while operating on the brain tissue using the surgical microscope. Information from both confocal endomicroscope 110 and surgical microscope 150 can be displayed to the surgeon simultaneously, facilitating resection of the tumor tissue.

Confocal endomicroscope 110 includes an endoscope 120, a radiation source 140 (e.g., a laser), and an imaging system 130. Radiation source 140 delivers radiation to brain tissue 101 through endoscope 120, while imaging system 130 provides an operator with images of the brain tissue based on radiation from the brain tissue (e.g., radiation produced by fluorescence of the ICG in the brain tissue).

Confocal endomicroscope 110 is configured for operation with ICG. In other words, radiation source 140 provides radiation at a wavelength (or wavelengths) that correspond to the absorption band of ICG. For example, radiation source 140 can provide radiation in wavelength range from 600 nm to 900 nm (e.g., 780 nm to 810 nm).

Radiation source 140 can be a laser or non-laser source. Radiation source 140 can be a near infrared (NIR) source (e.g., emitting wavelengths in a range from 0.7 μm to 1 μm).

Confocal endomicroscope 110 includes optical components to deliver radiation from radiation source 140 to brain tissue 101, and to deliver radiation from brain tissue 101 to imaging system 130. For example, endomicroscope 110 can include fiber waveguides (e.g., a bundle of optical fibers), lenses, beam splitters, wavelength filters, and/or detectors to deliver radiation to brain tissue 101 and image brain tissue 101 based on radiation emitted and/or reflected from brain tissue 101. Components used to deliver radiation from brain tissue 101 to imaging system 130 are selected to operate at a wavelength (or wavelengths) at which ICG fluoresces. Imaging system 130 includes a detector to detector radiation from the endomicroscope optical components and an electronic display which displays images of brain tissue 101 based on radiation collected by endomicroscope 110.

In some embodiments, confocal endomicroscope 110 includes a bundle of many optical fibers (e.g., several thousand optical fibers). Radiation from radiation source 140 is scanned across the proximal end of the fibers, which results in the laser light only travelling through the core of only 1 fiber at any instant in time. When the distal tip of the bundle is placed in contact with the tissue, each individual fiber makes a discrete fluorescence intensity measurement. Imaging system 130 collects a signal from each optical fiber and forms an image from the collected signals. An explanation of confocal microscopy using optical fiber bundles can be found in. Fiber-Optics in Scanning Optical Microscopy. *In Handbook of biological confocal microscopy*, by Delaney & Harris, 3rd Edition, Ed J. B. Pawley, 2006, Springer. pp 501-515.

In general, confocal endomicroscopy refers to the use of miniaturized point scanning confocal microscopes to examine the microscopic structures of tissue in vivo. Confocal endomicroscope 110 is small enough to be introduced into the body either through natural orifices or using minimally invasive techniques whereby an endomicroscope probe is introduced via a very small incision. Endomicroscopy can enable in vivo histology of the brain tissue without taking biopsies. Examples of confocal endomicroscopes are shown, for example, in U.S. Pat. Nos. 7,330,305 and 7,267,647, the entire contents both of which are incorporated herein by reference.

Confocal endomicroscope 110 has higher resolution than surgical microscope 150 but has a field of view that is substantially smaller than that of surgical microscope 150. For example, confocal endomicroscope 110 can have a resolution sufficiently high to resolve individual cells of the brain tissue. In some embodiments, confocal endomicroscope 110 has a lateral resolution of 5 μm or less (e.g., 2 μm or less, 1 μm or less, 0.7 μm or less, 0.5 μm or less). Confocal endomicroscope 110 can have an axial resolution (i.e., an optical slice thickness) of 10 μm or less (e.g., 7 μm or less, 5 μm or less).

Typically, the field of view of confocal endomicroscope 110 is 1 $mm^2$ or less (e.g., 0.5 $mm^2$ or less, 0.2 $mm^2$ or less, 0.1 $mm^2$ or less). Surgical microscope 150 is a microscope designed to be used in a surgical setting.

Generally, surgical microscope 150 includes one or more objectives providing magnification in a range from about 4× to about 50×. Surgical microscope 150 can have a field of view having an area of 1 $cm^2$ or more (e.g., 2 $cm^2$ or more, 5 $cm^2$ or more). Surgical microscope 150 is configured for fluorescence microscopy using ICG. Accordingly, it includes a radiation source for illuminating brain tissue 101 with radiation that causes ICG in the tissue to fluoresce. Surgical microscope 150 also include a camera capable of detecting radiation at the fluorescence wavelengths of ICG. In some embodiments, surgical microscope 150 includes a filter positioned between the camera and brain tissue 101 that blocks certain radiation emanating from the tissue from reaching the camera. For example, surgical microscope can include a high-pass filter than blocks radiation at wavelengths of about 800 nm or less, but transmits a band of wavelengths above 800 nm In general, a variety of surgical microscopes can be used. Examples of surgical microscopes include those commercially available from Carl Zeiss Meditec, Inc., USA, including those microscopes sold under the OPMI model range (e.g., OPMI Pentero C, OPMI Pentero, OPMI Neuro/NC4, OPMI Neuro MultiVision, OPMI Vario/NC33, OPMI Vario/588, OPMI pico/S100). In some embodiments, surgical microscope 150 is an OPMI Pentero configured for imaging radiation in the near infrared (e.g., 800 nm to 850 nm).

Figure 5:
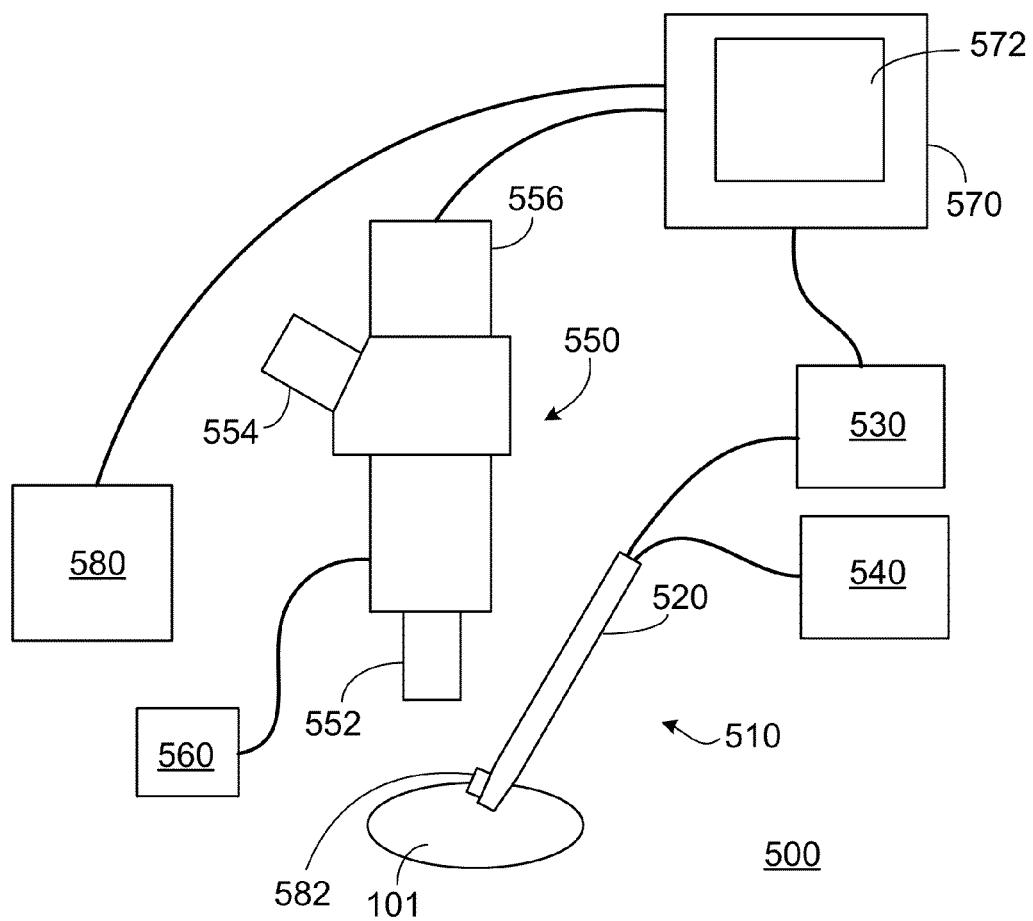
FIG. 5 is a schematic diagram of an embodiment of a microscopy system that includes a navigation subsystem.

In some embodiments, the microscopy system can include a navigation sub-system to facilitate tracking of locations of the brain tissue sampled using the endomicroscope. For example, referring to FIG. 5, a microscopy system 500 includes a navigation sub-system including a tracking module 580 and a probe 582 in addition to a confocal endomicroscope 510 and a surgical microscope 550. Probe 582 is attached to a handpiece 520 at or near a distal end of the endomicroscope. Tracking module 580 tracks the location of the distal end of the handpiece by tracking the location of probe 582.

In general, a variety of navigation sub-systems can be used. For example, custom and/or commercially available navigation sub-systems can be used. Navigation sub-systems are available, for example, from Medtronics. For example, in somne embodiments, the navigation sub-system is a Stealth-Station® AxiEM™ surgical navigation system from Medtronics, which works by generating an electromagnetic field around the patient's target anatomy that can be tracked to triangulate the positioning of instruments and patient-tracking devices during surgical navigation procedures. Navigation sub-systems are also available from BrainLab.

Confocal endomicroscope 510 also includes a radiation source 540 and an imaging system 530, which includes a detector. Surgical microscope 550 includes an objective 552, an eyepiece 554, and a camera 556. Tracking module 580, camera 556, and imaging system 530 are in communication with a display sub-system 570, which includes a display panel 572. Display sub-system 570 is displays image information from camera 556 and imaging system 530 on display panel 572 and uses information from tracking module 580 to provide information about the relative location of images acquired using the confocal endomicroscope and the field of view of the surgical microscope.

Figure 6:
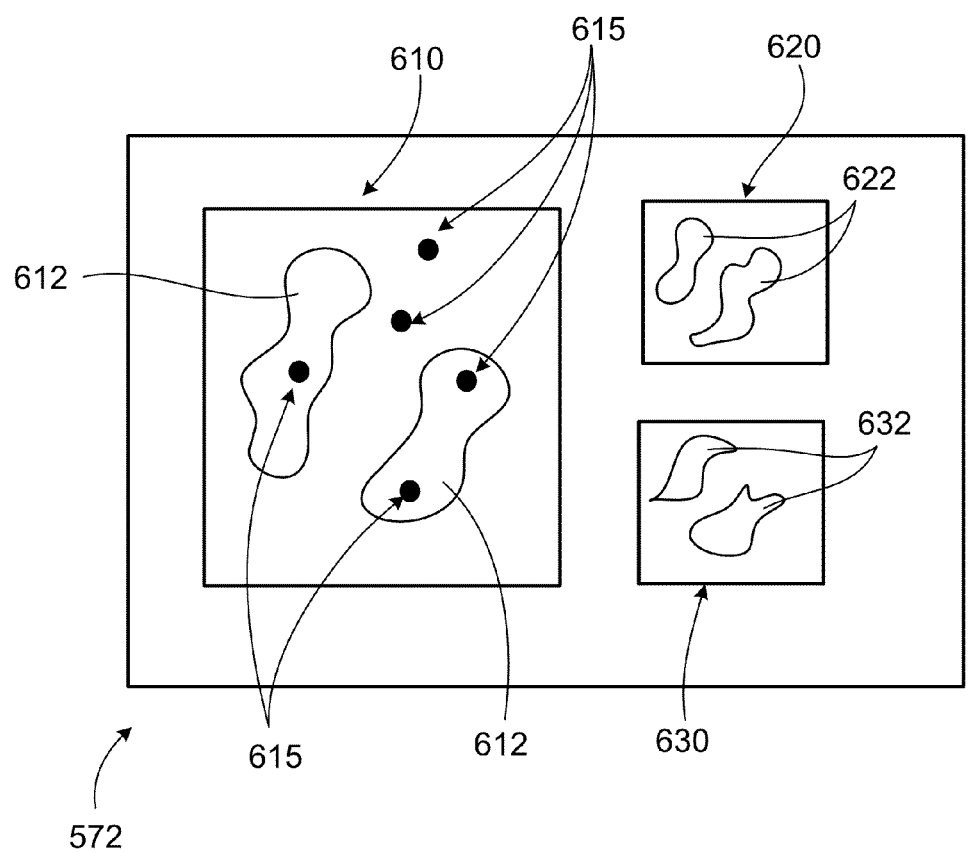
FIG. 6 is a schematic diagram showing images acquiring using a microscopy system.

For example, referring to FIG. 6, in some embodiments the display sub-system can simultaneously display images from both surgical microscope 550 and confocal endomicroscope 510. Here, display panel 572 shows a single image 610 of the field of view of surgical microscope. Alongside image 610 are two images 620 and 630 acquired using the confocal endomicroscope. Image 610 shows macroscopic structure 612 based on ICG fluorescence from the brain tissue in the field of view the surgical microscope. Images 620 and 630 show microscopic structure 622 and 632 (e.g., in which individual cells are resolved), respectively.

The display sub-system uses information from the navigation sub-system to show in image 610 information about the locations where images were acquired using the confocal endomicroscope. Specifically, image 610 shows five locations 615 relative to the macroscopic structure 612 in the image, identifying where confocal endomicroscope images were acquired. Images 620 and 630 correspond to the images acquired at two of these locations. The display sub-system can include an input device (e.g., a mouse, keyboard, or touchscreen) that allows a user to select which confocal endomicroscopic images are displayed. More or fewer than two of these images can be displayed at any time. While the confocal endomicroscopic images are displayed side-by-side with the macroscopic image, other ways of displaying this information is also possible (e.g., the images can be displayed picture-in-picture or on a separate display panel).

ICG is a near-infrared (NIR) fluorescent tricarbocyanine dye ($C_{43}H_{47}N_2NaO_6S_2$). With absorption and emission peaks between 805 and 835 nm respectively, the dye lies within the "optical window" of tissue where absorption attributable to endogenous chromophores is low (see, e.g., G. R. Chemick, S. W. Stein, C. M. Leevy, C. S. Davidson, *J Clin Invest* 39, 592 (April, 1960) and J. V. Frangioni, *Curr Opin Chem Biol* 7, 626 (October, 2003)). After intravenous injection, ICG binds almost completely to globulins, preferentially to α1-lipoproteins, within 1 to 2 seconds (see, e.g., K. J. Baker, *Proc Soc Exp Biol Med* 122, 957 (August-September, 1966)). When normal vascular permeability is preserved, the dye remains in the intravascular compartment. ICG has a plasma half-life of 3 to 4 minutes. After 10 minutes, only a small fraction of the originally injected volume can be detected in the blood. ICG is not metabolized in the body, and hepatic elimination is the main source of clearance.

ICG has been used extensively in retinal angiography and, more recently, in the intraoperative assessment of blood flow and patency in cerebrovascular surgery (see, e.g., A. Raabe, J. Beck, R. Gerlach, M. Zimmermann, V. Seifert, *Neurosurgery* 52, 132 (January, 2003)). It is believed that ICG is one of the least toxic substances ever administered to humans (see, e.g., J. V. Frangioni, *Curr Opin Chem Biol* 7, 626 (October, 2003)). The usual dose for videoangiography ranges between 0.2 and 0.5 mg/kg, and the total daily dose should not exceed 5 mg/kg (S7). In our study, all mice received a standard dose of 0.4 mg/kg ICG (Akorn, Inc., Buffalo Grove, Ill.) administered intravenously into the tail vein immediately after the brain convexity was exposed.

Indocyanine green (ICG), a near-infrared (NIR) wavelength contrast, has been used for videoangiography employing commercially available surgical microscopes equipped with appropriate optics. Investigation of ICG for macroscopic delineation of tumor margins (see, e.g., M. M. Haglund, M. S. Berger, D. W. Hochman, *Neurosurgery* 38, 308 (February, 1996)) demonstrated encouraging specificity for tissue containing tumor but required timed measurements that limits interactivity in the surgical workflow and precludes rapid screening of multiple observational fields. Confocal endomicroscopy has enabled histologic tissue identification in human gynecologic endoscopic, laparoscopic applications and gastrointestinal endoscopy, employing VWF contrast (see, e.g., R. Kiesslich et al., *Gastroenterology* 127, 706 (2004)). A miniaturized confocal endomicroscope was recently developed for NIR imaging of ICG. NIR confocal microscopy of ICG has not previously been assessed for intraoperative microscopic detection of cancer. Intraoperative ICG confocal endomicroscopy was tested as a tool to identify infiltrating brain tumor cells and tumor margins.

Thirty mice implanted with glioblastoma cells underwent craniectomies for exposure of tumors 14 days implantation. Tumors were clearly visible macroscopically and extended from cortical surface to deep basal brain structures. ICG was then administered using 0.4 mg/kg, equivalent to a standard single dose for humans (see, e.g., I. Roberts et al., *Lancet* 342, (1993)). Intraoperative confocal endomicroscopy of ICG distribution revealed striking microvascular, cellular and subcellular structures in various tumor regions that correlated with conventional histology and known tissue architecture. Applying the confocal probe to normal-appearing brain distant from the tumor revealed a predominantly intravascular ICG distribution, strongly contrasting bright small vessels and capillary networks over a dark extravascular background, and extravascular ICG staining sparsely distributed among uniformly shaped cell bodies morphologically consistent with the histology of normal brain tissue. Erythrocyte streaming was observed in vessels during continuous imaging. Immediately after ICG injection, fluorescence was seen only in a few clusters of tumor cells. Fifteen minutes later the entire tumor mass was saturated with ICG expressing bright fluorescence of tumor cells. Within obvious tumor tissue, images were dominated by extravascular ICG concentrated in clusters of cellular structures showing hypercellularity and pleomorphism, morphologically consistent with cytoplasmic labeling of tumor cells. Other regions presented a complex mixture of these patterns, with mostly normal-appearing brain punctuated by large pleomorphic cells consistent with an infiltrative margin or satellite tumor cell clusters surrounded by brain tissue. Importantly, patterns consistent with tumor morphology were also seen in brain tissue neighboring the tumor that appeared macroscopically normal as viewed via the surgical microscope. Critically, individual tumor cells within brain tissue could be identified within 475×475 μm field of view and a definitive tumor border delimited (FIGS. 2A-2D).

Macroscopic fluorescence was effective for gross tumor detection, but ICG microscopy greatly enhanced the sensitivity of the macroscopic observations and provided real-time histological information precisely related to the site of microscopic imaging. These data suggest that combined macroscopic and microscopic in vivo ICG imaging could allow the interactive identification of tumor areas and the extent of microscopic tumor cell infiltration into the brain, substantially improving intraoperative decisions during the resection of malignant gliomas.

Additional details of the study follow.

Animals

Female B6 (Cg)-Tyr$^{c-2J}$/J (albino variant of C57BL/6) mice (10-12 weeks age) were obtained from The Jackson Laboratory, Bar Harbor, Me. The mice were kept in the animal care facility of St. Joseph's Hospital and Medical Center in rooms with controlled temperature and humidity under a 12-hour light-dark cycle. The animals were provided with standard rodent chow and water ad libitum. Experiments were performed in accordance with the guidelines and regulations set forth by the National Institutes of Health Guide for the Care and Use of Laboratory Animals and were approved by the Institutional Animal Care and Use Committee at the Barrow Neurological Institute and St. Joseph's Hospital and Medical Center.

Brain Tumor Model

The GL261 cell line was obtained from the Division of Cancer Treatment and Diagnosis (DCTD) of the National Cancer Institute (NCI), Frederick, Md. This GL261 cell line was created from a mouse brain tumor originally induced by intracranial injection of 3-methyl-cholantrene into the C57BL/6 syngeneic mouse strain (see, e.g., D. Zagzag et al., Lab Invest 80, 837 (June, 2000)). The morphological, biochemical and growth characteristics of the GL261 mouse brain tumor model have been described elsewhere (see, e.g., M. Candolfi et al., J Neurooncol 85, 133 (November, 2007) and T. Szatmari et al., Cancer Sci 97, 546 (June, 2006)). To facilitate a quantitative measurement of the tumor growth rate, GL261 cells were made bioluminescent using the Lentiphos™ HT System (Clontech Laboratories, Inc., Mountain View, Calif.) with the Lenti-X™ HT Packaging Mix (Clontech Laboratories, Inc.) and the FUW-GL plasmid (a generous gift from the laboratory of J. B. Rubin, MD, PhD). The resulting GL261-luc cells were grown in Dulbecco's modified eagle's medium (DMEM, Invitrogen, Carlsbad, Calif.) supplemented with 10% tetracycline-free fetal calf serum (Clontech Laboratories, Inc) at 37° C. with 5% $CO_2$. Cultured cells were harvested by trypsinization, washed once in phosphate-buffered saline (Invitrogen, Carlsbad, Calif.), and resuspended in DMEM without serum at a concentration of $1 \times 10^7$ cells/mL.

Intracranial Implantation

Animals were anesthetized by intraperitoneal injection of a mixture of 10 mg/kg xylazine and 80 mg/kg ketamine (Wyeth, Madison, N.J.). A 10-mm incision was made starting between the animal's eyes, exposing the bregma. A bur hole was made 0.1 mm posterior to the bregma and 2.3 mm right of the midline using a small animal stereotactic headframe (Model 900, David Kopf Instruments, Tujunga, Calif.). Cells were infused at a total depth of 2.0 mm below the surface of the brain after the syringe (World Precision Instruments, Sarasota, Fla.) was advanced 2.5 mm to create a 0.5-mm pocket. The cell suspension was infused over 3 minutes using a UMP3-1 UltraMicroPump microinjector (WPI, Sarasota, Fla.) set to a volume of 2 µL with an infusion rate of 0.67 µL/minute. The needle was withdrawn 2 minutes after the injection to minimize backflow of the cell suspension. The bur hole was covered with bone wax and the skin incision was sutured.

Tumor Growth

Intracranial tumor growth was analyzed by in vivo bioluminescent imaging using an IVIS® Spectrum in vivo imaging system (Caliper Life Sciences, Hopkinton, Mass.). Animals were injected subcutaneously with luciferin (15 mg/mL in PBS, 150 µg luciferin/kg body weight; Caliper Life Sciences) 20 minutes before imaging. Animals were anesthetized with isoflurane and maintained at 37° C. under isofluorane anesthesia during the imaging process. Tumor cells were detectable from the day of implantation, and quantitation was done using the imaging system's Living Image® 3.1 software. Quantitative measurements of the tumor burden were reproducible in that they rose steadily until the fourteenth day after implantation. However, growth curves mostly depended on the state of implanted cells, unavoidable minor variability in the implantation procedure, or both.

Animal Surgery

On the fourteenth day after implantation, mice were anesthesized using the xylazine/ketamine mixture as described previously and underwent craniectomy for exposure of convexital surfaces of both cerebral hemispheres and intraoperative imaging. Oxygen supply and body temperature were maintained during the procedure. Intraparenchymal brain tumors were macroscopically identified in the right hemisphere of all implanted mice. Successful hemostasis was achieved throughout the procedure with saline irrigation. At the end of each experiment, anesthetized animals were euthanized according to our institutional guidelines.

Study Design

This study was conducted in two main phases. The purpose of the first phase was to validate the use of ICG fluorescence in both intraoperative NIR macroscopic and miniaturized confocal endomicroscopic techniques for the identification of brain tumors in the mouse model. The first phase of the experiment was conducted on 18 mice. Several intraoperative fluorescence macroscopic video loops, confocal images, and histological specimens were collected and analyzed from each mouse. The second phase was conducted to determine the timing characteristics of brain tumor saturation with ICG, both macro- and endomicroscopically. Two cohorts of animals were used in the second phase: (1) six mice were used for intraoperative fluorescence macroscopy and (2) six mice were used for intraoperative confocal endomicroscopy.

Phase One

Intraoperative Fluorescence Macroscopy

Figure 3:
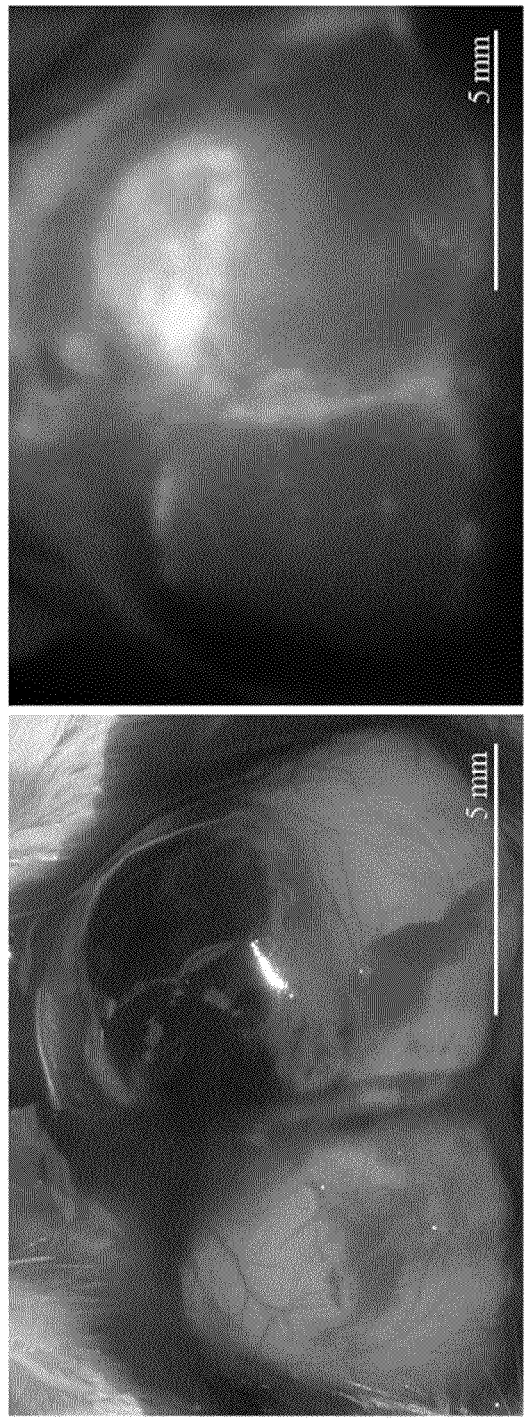
FIGS. 3(A) and 3(B) show macroscopic intraoperative views of a B6 (Cg)-Tyrc-2J/J mouse brain tumor 14 days after stereotactic implantation of GL261-luc glioma cells. A large necrotic mass with significant peritumoral edema abuts the surface of the right frontal lobe under regular white light (left). After the ICG was injected, the tumor was macroscopically visible with NIR light and is delineated by an intense, heterogeneous central fluorescent region and a less bright peripheral halo. Intravascular ICG denotes vessels (right).

A neurosurgical microscope with built-in NIR videoangiography technology (Zeiss OPMI Pentero; Carl Zeiss Surgical, GmbH., Oberkochen, Germany) was used for intraoperative macroscopic imaging. The device integrates NIR imaging into the surgical microscope, capturing high-resolution NIR images based on ICG fluorescence without eliminating visible light during the entire surgical intervention (range of magnification 1.2-14.6×) (see, e.g., A. Raabe, J. Beck, R. Gerlach, M. Zimmermann, V. Seifert, *Neurosurgery* 52, 132 (January, 2003)). Once exposed, the mouse brain was illuminated by the NIR light emitted from the surgical microscope. An optical filter built into the microscope imaging system blocked both ambient and excitation light so that only ICG-induced fluorescence was captured. Immediately after intravenous injection, ICG fluorescence could be observed in major vessels. (FIG. 3A-3B).

Intraoperative Confocal Endomicroscopy

Intraoperative confocal endomicroscopy was accomplished using a prototype handheld instrument in which a miniaturized scanner has been integrated into a rigid probe with 6.3 mm outer diameter, providing a working length of 150 mm (Optiscan Pty. Ltd., Victoria, Australia). A 780-nm diode laser provided incident excitation light, and fluorescent emission was detected at >795 nm using a long-pass filter, both via a single optical fiber acting as the excitation and detection pinholes for confocal isolation of the focal plane. The detector signal was digitized synchronously with the scanning to construct images parallel to the tissue surface (en face optical sections). Laser power was typically set to 550-900 W at brain tissue; maximum power was limited to 2000 W. A field of view of 475×475 µm (approximately 1000× magnification on a 21-inch screen) was scanned either at 1024×512 pixels (at 1.2/s frame rate) or 1024×1024 pixels (0.7/s frame rate). The resulting images were stored digitally and could be recorded as video loops. During the procedure, a foot pedal provided remote control of the variable confocal imaging plane depth from the surface to a depth >350 µm. After ICG was injected, the miniaturized probe affixed to the stereotactic head frame was moved gently along the surface of the brain tissue to obtain images from several regions of interest (ROIs). ROIs included normal brain and regions of obvious tumor in addition to the transitional zone between normal brain and tumor. The mechanical shaft of the stereotactic frame was used to move the probe smoothly between different ROIs without losing contact with the tissue. Several images were acquired from each ROI at the surface and at increasing depths of the tissue. Unique aspects of individual cells and other surrounding tumor tissue were seen as the endomicroscopic probe images throughout its focal depth range (Video). The total imaging time was about 40 minutes per mouse with the animal in optimal physiologic status.

Tissue Sampling, Histology, and Data Processing

Multiple biopsy samples were harvested from each mouse. Brain tissues slices (0.5 cm$^2$) containing several ROIs were cut manually parallel to the surface. Areas that were imaged using a confocal endomicroscope were marked with tissue ink (Pathmark, BBC Biochemical, Mount Vernon, Wash.) so that precise locations of confocal endomicroscopic imaging could be validated with conventional histology. The tissue was placed in a cassette for standard formalin fixation and paraffin embedding. Histologic assessment was performed using standard light microscopic evaluation of 10-μm thick hematoxylin and eosin (H&E)-stained sections. Careful labeling and grouping of acquired confocal images and specific biopsy samples ensured correct correlation. Image sequences were collated into video loops and confocal images were evaluated using ImageJ software (see, e.g., W. S. Rasband. (U.S. National Institutes of Health, Bethesda, Md., USA, 1997-2009)).

Phase Two

Figure 4:
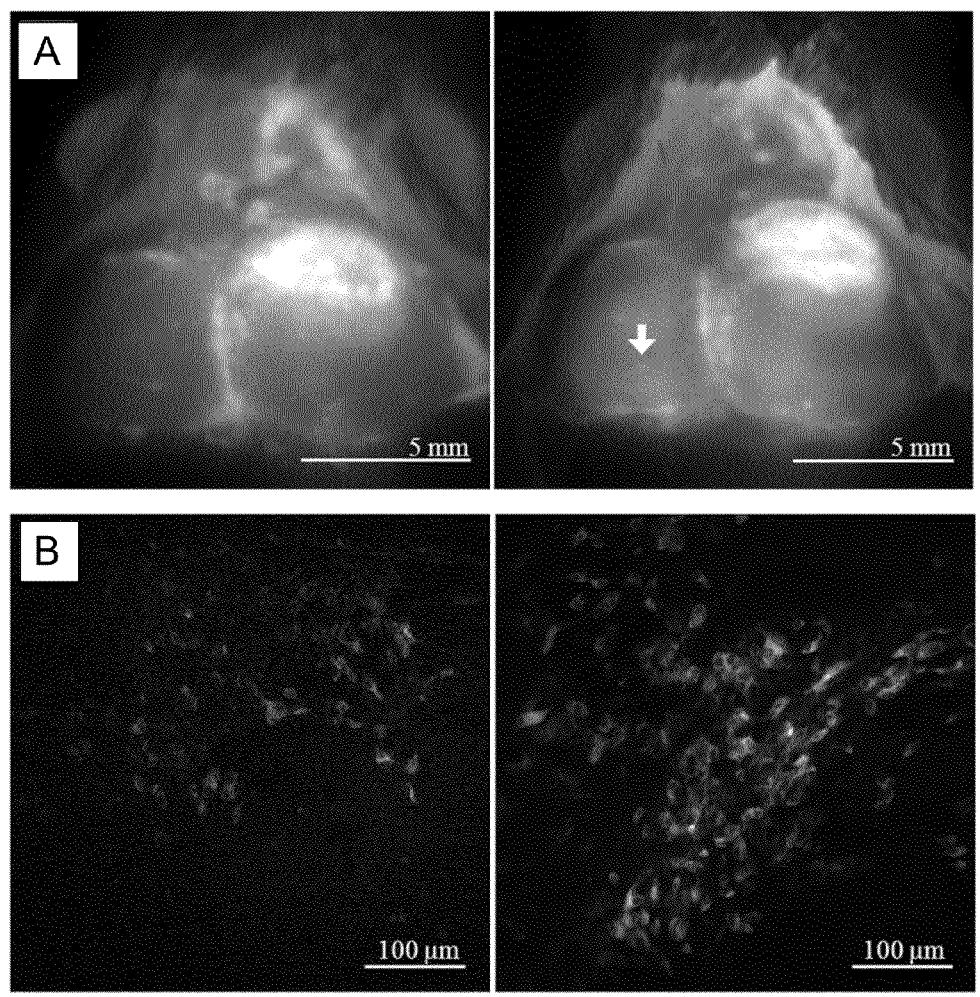
FIGS. 4(A)-4(B) are photographs showing timing characteristics of brain tumor saturation with ICG.

Mice from both cohorts were imaged for 15 minutes after the ICG was injected. Continuous video recording using both white light and NIR modes allowed the kinetics of macroscopic tumor size and fluorescence in the first cohort to be assessed. Mice from the second cohort underwent intraoperative confocal endomicroscopy with the miniaturized probe being placed above obvious tumor tissue. Images were acquired from the same ROI in a sequential fashion over 15 minutes, and data from different time points were compared (FIG. 4A-4B). Interestingly, some regions of focal brightness viewed in fluorescent mode under a surgical microscope were morphologically consistent with normal brain on confocal endomicroscopy, mostly representing leakage of ICG related to surgical trauma.

While the aforementioned systems are discussed for use with ICG, more generally, the systems can be adapted for use with other dyes and/or at other fluorescent wavelengths.

Moreover, while the aforementioned example is with respect to brain surgery, the techniques disclosed herein can be applied in other fields of medicine, such as those that make significant use of the operating microscope (e.g, dentistry (especially endodontics), ENT surgery, and opthalmic surgery).

Furthermore, while the aforementioned embodiments feature a surgical microscope for providing a macroscopic image of the tissue under study, other types of microscope can be used. For example, in some embodiments, the macroscopic images can be acquired using a second endomicroscope.

Accordingly, other embodiments are within the scope of the following claims.

What is claimed is:

1. A microscopy system, comprising:
   a surgical microscope having a first field of view configured to acquire images of a sample within the first field of view when the sample is exposed to infrared radiation;
   a confocal endomicroscope having a second field of view configured to acquire images of the sample within the second field of view;
   a navigation sub-system configured to monitor a location of the second microscope; and
   a display sub-system in communication with the first microscope, the second microscope and the navigation sub-system,
   wherein:
      the surgical microscope has a field of view having an area of 1 cm$^2$ or more;
      the area of the field of view of the confocal endomicroscope is 1 mm$^2$ or less; and
      during operation of the microscopy system the display sub-system displays information about a relative location of one or more images acquired using the confocal microscope relative to the field of view of the surgical microscope based on information from the navigation sub-system.

2. A method, comprising:
   providing the system of claim 1,
   introducing indocyanine green into a patient; and
   using the confocal endomicroscope to detect a tumor in brain tissue of the patient based on fluorescence from the indocyanine green.

3. The method of claim 2, further comprising using the surgical microscope to observe the brain tissue concurrently with using the confocal endomicroscope.

4. The method of claim 2, further comprising performing surgery on the brain tissue concurrently with using the confocal endomicroscope.

5. The method of claim 2, wherein detecting the tumor comprises identifying individual tumor cells using the confocal endomicroscope.

6. The method of claim 2, wherein using the confocal endomicroscope comprises illuminating the brain tissue with radiation.

7. The method of claim 6, wherein the radiation is near infrared (NIR) radiation.

8. The method of claim 2, wherein detecting the tumor comprises imaging the brain tissue at an emission wavelength of indocyanine green.

9. The method of claim 2, wherein detecting the tumor comprises identifying individual tumor cells based on fluorescence from the indocyanine green in the brain tissue.

10. The method of claim 2, wherein detecting the tumor comprises delimiting a border of the tumor based on fluorescence from the indocyanine green in the brain tissue.

11. A method, comprising:
    providing the system of claim 1;
    introducing indocyanine green into a patient;
    using the confocal endomicroscope to detect a tumor in brain tissue of the patient based on fluorescence from the indocyanine green;
    using the surgical microscope to observe the brain tissue concurrently with using the confocal endomicroscope; and
    performing surgery on the brain tissue concurrently with using the confocal endomicroscope.

12. The system of claim 1, wherein the surgical microscope has a field of view having an area of 2 cm$^2$ or more.

13. The system of claim 1, wherein the surgical microscope comprises an infrared camera.

14. The system of claim 1, wherein the surgical microscope is a fluorescence microscope.

15. The system of claim 14, wherein the surgical microscope is configured to detect radiation at wavelengths of 800 nm or more.

16. The system of claim 15, wherein the surgical microscope is configured to detect radiation at one or more wavelengths corresponding to fluorescence wavelengths of indocyanine green.

17. The system of claim 16, wherein the surgical microscope comprises a camera and a filter positioned in an optical path between the sample and the detector, the filter being configured to transmit radiation at one or more wavelengths corresponding to fluorescence wavelengths of indocyanine green.

18. The system of claim 1, wherein the confocal endomicroscope comprises a detector and a bundle of optical fibers configured to deliver radiation from the sample to the detector.

19. The system of claim 1, wherein the area of the field of view of the confocal endomicroscope is 0.5 mm$^2$ or less.

20. The system of claim 1, wherein the confocal endomicroscope is configured to detect radiation at wavelengths of 800 nm or more.

21. The system of claim 20, wherein the confocal endomicroscope is configured to detect radiation at one or more wavelengths corresponding to fluorescence wavelengths of indocyanine green.

22. The system of claim 1, wherein the sample is a tissue sample and the confocal endomicroscope has a resolution sufficient to resolve individual cells in the sample.

23. The system of claim 1, wherein the navigation sub-system comprises one or more probes attached to the second microscope.

24. The system of claim 1, wherein the display sub-system is configured to simultaneously display one or more image of the sample from the surgical microscope and one or more image of the sample from the confocal endomicroscope.

25. The system of claim 1, wherein the display sub-system is configured to display locations in an image acquired by the surgical microscope where images were acquired using the confocal endomicroscope based on information from the navigation sub-system.

26. The system of claim 1, wherein the surgical microscope comprises an objective.

27. A microscopy system, comprising:
   a first microscope having a first field of view configured to acquire images of a sample within the first field of view when the sample is exposed to infrared radiation;
   a second microscope having a second field of view configured to acquire images of the sample within the second field of view;
   a navigation sub-system configured to monitor a location of the second microscope; and
   a display sub-system in communication with the first microscope, the second microscope and the navigation sub-system,
   wherein:
      the first microscope is different from the second microscope;
      the first microscope comprises an objective;
      the first microscope has a field of view having an area of 1 cm$^2$ or more;
      the area of the field of view of the second microscope is 1 mm$^2$ or less; and
      during operation of the microscopy system the display sub-system displays information about a relative location of one or more images acquired using the second microscope relative to the field of view of the first microscope based on information from the navigation sub-system.

* * * * *

UNITED STATES PATENT AND TRADEMARK OFFICE
CERTIFICATE OF CORRECTION

Page 1 of 1

PATENT NO. : 9,044,142 B2
APPLICATION NO. : 13/043120
DATED : June 2, 2015
INVENTOR(S) : Hauger et al.

It is certified that error appears in the above-identified patent and that said Letters Patent is hereby corrected as shown below:

On the title page, item [56], col. 2, line 1, under "OTHER PUBLICATIONS", delete "infared" and insert -- infrared --.
In the specification
Col. 4, line 39, delete "subsystem." and insert -- sub-system. --.
Col. 5, line 42, delete "in." and insert -- in --.
Col. 6, line 45, delete "somne" and insert -- some --.
Col. 7, line 28, delete "Chemick," and insert -- Cherrick, --.
Col. 9, line 52, delete "isofluorane" and insert -- isoflurane --.
Col. 9, lines 62-63, delete "anesthesized" and insert -- anesthetized --.
Col. 10, line 52, delete "W" and insert -- µW --.
Col. 10, line 53, delete "W." and insert -- µW. --.

Signed and Sealed this
Twenty-sixth Day of April, 2016

Michelle K. Lee
*Director of the United States Patent and Trademark Office*